(12) United States Patent
Kim et al.

(10) Patent No.: US 12,029,482 B2
(45) Date of Patent: Jul. 9, 2024

(54) OPTICAL COHERENCE TOMOGRAPHY SYSTEM FOR OCULAR DIAGNOSIS

(71) Applicant: Korea University Research and Business Foundation, Seoul (KR)

(72) Inventors: Beop-Min Kim, Seoul (KR);
Hyung-Jin Kim, Anyang-si (KR);
Byeong-Joo Song, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 726 days.

(21) Appl. No.: 17/034,356

(22) Filed: Sep. 28, 2020

(65) Prior Publication Data
US 2021/0219837 A1    Jul. 22, 2021

(30) Foreign Application Priority Data
Jan. 22, 2020 (KR) ........................ 10-2020-0008557

(51) Int. Cl.
*A61B 3/10* (2006.01)
*A61B 3/00* (2006.01)

(52) U.S. Cl.
CPC ............ *A61B 3/102* (2013.01); *A61B 3/0008* (2013.01)

(58) Field of Classification Search
CPC ............................... A61B 3/102; A61B 3/0008
(Continued)

(56) References Cited

U.S. PATENT DOCUMENTS

2012/0327423 A1* 12/2012 Hanebuchi ......... G01B 9/02019
356/497
2013/0301033 A1* 11/2013 Alarousu ........... G01B 9/02044
356/51
(Continued)

FOREIGN PATENT DOCUMENTS

EP    2 869 020 A1    5/2015
KR    10-1287289 B1    7/2013
(Continued)

OTHER PUBLICATIONS

Communication dated Dec. 8, 2020 by the European Patent Office in application No. 20201124.3.
(Continued)

*Primary Examiner* — Sharrief I Broome
(74) *Attorney, Agent, or Firm* — Sughrue Mion, PLLC

(57) ABSTRACT

An optical coherence tomography system for ocular diagnosis includes a light source unit generating and transmitting light, a light distribution unit dividing the transmitted light into first light and second light, a reference arm generating first reference light and second reference light, whose optical path length is larger than that of the first reference light, from the first light, a sample arm irradiating the second light onto a central optical axis directed towards the central portion of the eye lens to generate first measurement light and irradiating the second light onto the eye lens in an oblique direction inclined with respect to the central optical axis at a time different from the time when the first measurement light is generated, to generate second measurement light, an interference unit allowing the first reference light to interfere with the first measurement light and the second reference light to interfere with the second measurement light to generate corresponding interference signals, and a detection
(Continued)

unit converting the interference signals into electrical signals.

4 Claims, 6 Drawing Sheets

(58) Field of Classification Search
USPC .................... 351/220, 221, 233, 224, 200
See application file for complete search history.

(56) References Cited

U.S. PATENT DOCUMENTS

| 2014/0176903 A1* | 6/2014 | Qiu | A61B 3/1025 |
| | | | 351/206 |
| 2015/0201833 A1* | 7/2015 | Chong | G01B 9/02019 |
| | | | 351/206 |
| 2016/0045106 A1* | 2/2016 | Jaillon | G01B 9/02019 |
| | | | 351/221 |

FOREIGN PATENT DOCUMENTS

| WO | 2017/135278 A1 | 8/2017 |
| WO | 2017137567 A1 | 8/2017 |

OTHER PUBLICATIONS

Communication dated Feb. 17, 2021 by the Korean Intellectual Property Office in application No. 10-2020-0008557.

* cited by examiner

OPTICAL COHERENCE TOMOGRAPHY SYSTEM FOR OCULAR DIAGNOSIS

BACKGROUND

1. Field

The present invention relates to an optical coherence tomography system for ocular diagnosis, and more specifically to an optical coherence tomography system that can acquire two- and three-dimensional images of the eye lens.

2. Description of Conventional Art

Recently, optical coherence tomography (OCT) has received attention in the industrial fields, including optical medical devices. OCT systems are diagnostic imaging devices for high-resolution imaging of internal microstructures in living tissue based on optical interference. OCT systems can acquire high-resolution sectional images of living tissue in a non-invasive manner and are thus used for clinical or therapeutic purposes in dermatology, ophthalmology, internal medicine, dentistry, and other medical specialties.

Particularly, the morphology and biometry of the anterior segment of the eye have been actively investigated based on OCT in the field of ophthalmology. In the case of corneal refractive surgery and intraocular lens implantation for cataract surgery, OCT can play a crucial role in accurate pretherapeutic diagnosis and observation of postoperative prognosis that impose a burden on patients. OCT-based studies on geometric changes in eye lenses during adaptation will provide a key direction for the treatment of presbyopia while understanding the precise mechanism of action of adaptation.

FIG. 1 shows an image of the eyeball obtained with an OCT system. Previous OCT-based studies on the anterior segment of the eye and the eye lens are limited to the regions except the peripheral portions of the eye lens hidden by the iris. This imposes restrictions on monitoring diseases in the portions hidden by the iris and observing changes in the overall morphology and shape of the eye lens. For intraocular lens implantation for cataract treatment, the correct position of an artificial eye lens at the maximum equatorial diameter of the eye lens has a significant influence on the improvement of patient's eyesight. However, these restrictions limit the use of OCT and techniques for quantifying the position of artificial eye lenses are still insufficient. Under such circumstances, most ophthalmologists check the position of artificial eye lenses with their own eyes, which is a defective operation.

Thus, there is an urgent need for a solution to the problems of conventional OCT systems.

SUMMARY

The present invention has been made in an effort to solve the problems of the prior art, and one aspect of the present invention is to provide an optical coherence tomography system for ocular diagnosis that irradiates light in an oblique direction toward the eye lens as well as in a direction perpendicular to the eye lens to acquire optical coherence tomography images of the whole eye lens.

An optical coherence tomography system for ocular diagnosis according to one embodiment of the present invention includes: a light source unit generating and transmitting light; a light distribution unit dividing the transmitted light into first light and second light; a reference arm generating first reference light and second reference light, whose optical path length is larger than that of the first reference light, from the first light; a sample arm irradiating the second light onto a central optical axis directed towards the central portion of the eye lens to generate first measurement light and irradiating the second light onto the eye lens in an oblique direction inclined with respect to the central optical axis at a time different from the time when the first measurement light is generated, to generate second measurement light; an interference unit allowing the first reference light to interfere with the first measurement light and the second reference light to interfere with the second measurement light to generate corresponding interference signals; and a detection unit converting the interference signals into electrical signals.

In the optical coherence tomography system, the reference arm may include: a first reference arm optical coupler dividing the first light transmitted from the light distribution unit into third light and fourth light; a first reference light output unit including a first reference arm optical fiber connected to the first reference arm optical coupler and through which the third light is transmitted, a first reference arm collimator arranged at one end of the first reference arm optical fiber, a second reference arm collimator spaced a first distance from the first reference arm collimator, and a second reference arm optical fiber whose one end is connected to the second reference arm collimator, and generating and outputting the first reference light from the third light; and a second reference light output unit including a third reference arm optical fiber connected to the first reference arm optical coupler and through which the fourth light is transmitted, a third reference arm collimator arranged at one end of the third reference arm optical fiber, a fourth reference arm collimator spaced a second distance larger than the first distance from the third reference arm collimator, and a fourth reference arm optical fiber whose one end is connected to the fourth reference arm collimator, and generating and outputting the second reference light from the fourth light.

In the optical coherence tomography system, the reference arm may further include a second reference arm optical coupler connected to the other end of the second reference arm optical fiber and the other end of the fourth reference arm optical fiber.

In the optical coherence tomography system, the reference arm may include: a light delivery unit including an optical circulator receiving the first light from the light distribution unit, a first reference arm optical fiber whose one end is connected to the optical circulator, and a reference arm collimator connected to the other end of the first reference arm optical fiber; a reference arm scanning mirror changing the direction of propagation of the first light exiting from the reference arm collimator; a first reflective mirror spaced a first distance from the reference arm scanning mirror and reflecting the first light incident from the reference arm scanning mirror back to the reference arm scanning mirror; and a second reflective mirror spaced a second distance larger than the first distance from the reference arm scanning mirror and reflecting the first light incident from the reference arm scanning mirror back to the reference arm scanning mirror.

In the optical coherence tomography system, the sample arm may include: a sample arm collimator connected to one end of an optical fiber through which the second light from the light distribution unit is transmitted; a sample arm scanning mirror continuously changing the direction of propagation of the second light exiting from the sample arm collimator; a first scanning lens through which the second light reflected from the sample arm scanning mirror is transmitted and whose curved central portion is arranged on the central optical axis; a first outwardly reflective mirror arranged between a curved peripheral portion surrounding the curved central portion of the first scanning lens and the eye lens to reflect the second light transmitted through the curved peripheral portion in a lateral direction outward from the eye lens; and a first reflection system reflecting the second light reflected from the first outwardly reflective mirror in a first oblique direction toward the eye lens from the outside of the eye lens.

In the optical coherence tomography system, the first reflection system may include: a first mirror reflecting the second light reflected from the first outwardly reflective mirror; a first lens through which the second light reflected from the first mirror is transmitted; a second mirror reflecting the second light transmitted through the first lens; a third mirror reflecting the second light reflected from the second mirror; a fourth mirror reflecting the second light reflected from the third mirror in the first oblique direction; and a second lens through which the second light reflected from the fourth mirror is transmitted.

In the optical coherence tomography system, the sample arm may further include: a second outwardly reflective mirror arranged so as to be symmetric to the first outwardly reflective mirror with respect to the central optical axis and reflecting the second light transmitted through the curved peripheral portion in a lateral direction outward from the eye lens; and a second reflection system reflecting the second light reflected from the second outwardly reflective mirror in a second oblique direction toward the eye lens from the outside of the eye lens.

In the optical coherence tomography system, the second reflection system may include: a first mirror reflecting the second light reflected from the second outwardly reflective mirror; a first lens through which the second light reflected from the first mirror is transmitted; a second mirror reflecting the second light transmitted through the first lens; a third mirror reflecting the second light reflected from the second mirror; a fourth mirror reflecting the second light reflected from the third mirror in the second oblique direction; and a second lens through which the second light reflected from the fourth mirror is transmitted.

The features and advantages of the present invention will become apparent from the following description with reference to the accompanying drawings.

Prior to the detailed description of the invention, it should be understood that the terms and words used in the specification and the claims are not to be construed as having common and dictionary meanings but are construed as having meanings and concepts corresponding to the technical spirit of the present invention in view of the principle that the inventor can define properly the concept of the terms and words in order to describe his/her invention with the best method.

The optical coherence tomography system of the present invention is constructed such that light is irradiated onto the eye lens in an oblique direction toward the eye lens as well as in a direction perpendicular to the eye lens. Due to this construction, the optical coherence tomography system of the present invention can generate measurement light by one-time scanning so that optical coherence tomography images of the whole anterior segment of the eye including peripheral portions hidden by the iris can be obtained.

Therefore, the optical coherence tomography system of the present invention can be used to accurately diagnose diseases of the anterior segment of the eye, show the morphology of the whole eye lens, and monitor the eye lens in real time. Due to these advantages, the optical coherence tomography system of the present invention can be utilized as a powerful diagnostic tool for observing prognosis of intraocular lens implantation.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
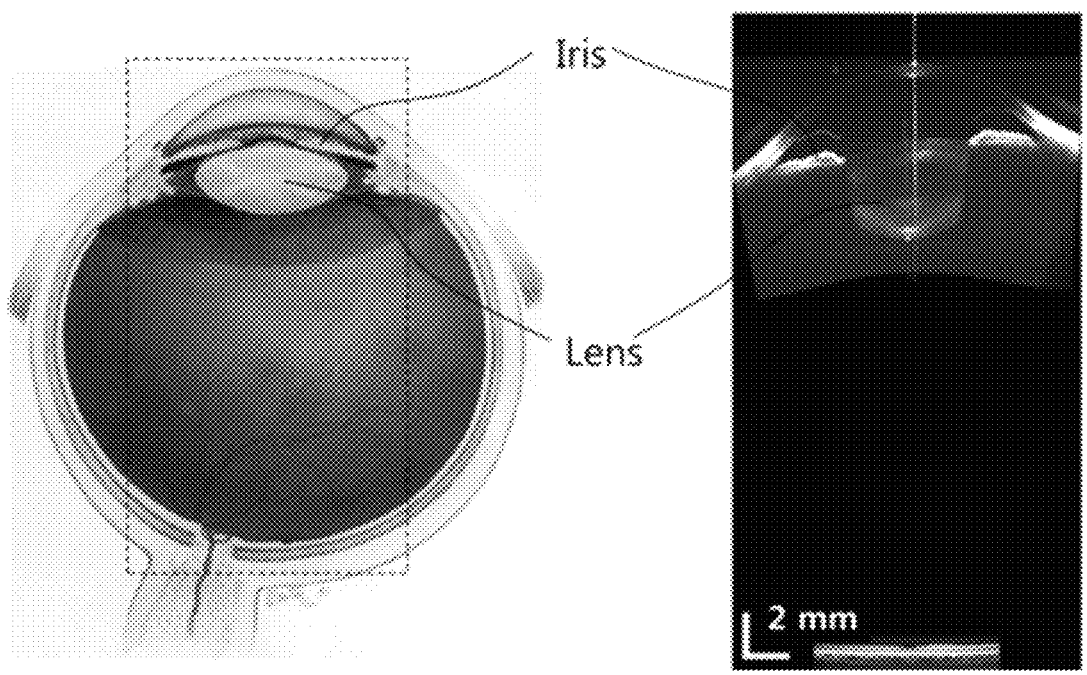
FIG. 1 shows an image of the eyeball obtained with a conventional optical coherence tomography (OCT) system.

Other objects, advantages, and novel features of the invention will become more apparent from the following detailed description and preferred embodiments with reference to the appended drawings. In the drawings, the same elements are denoted by the same reference numerals even though they are depicted in different drawings. In the description of the present invention, detailed explanations of related art are omitted when it is deemed that they may unnecessarily obscure the essence of the present invention.

Preferred embodiments of the present invention will now be described in detail with reference to the accompanying drawings.

Figure 2:
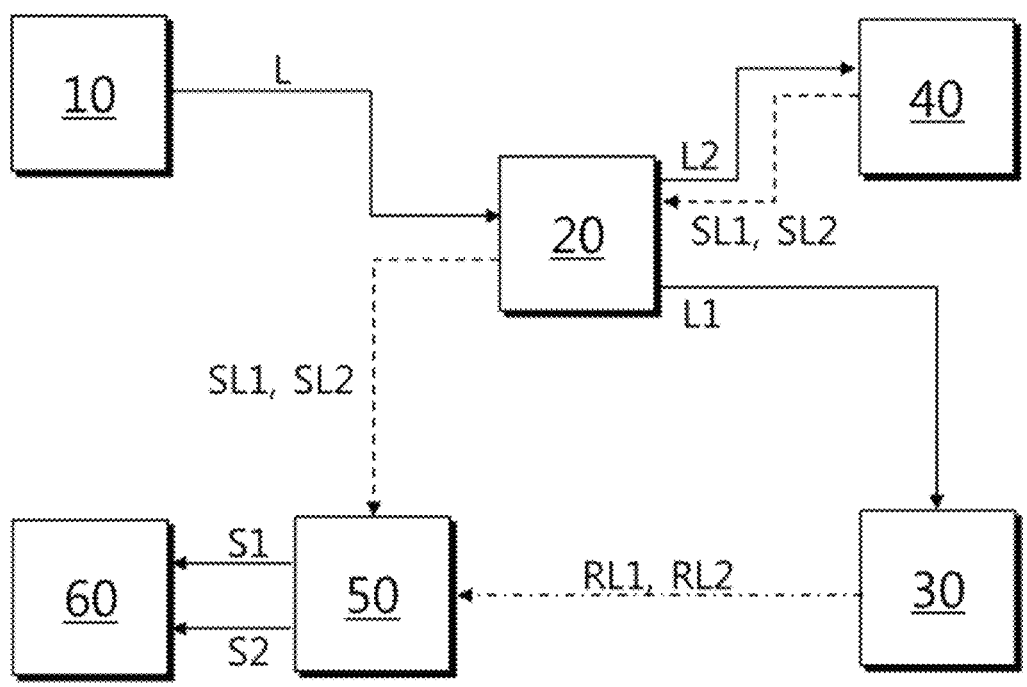
FIGS. 2 and 3 are block diagrams illustrating an optical coherence tomography system for ocular diagnosis according to one embodiment of the present invention.
Figure 3:
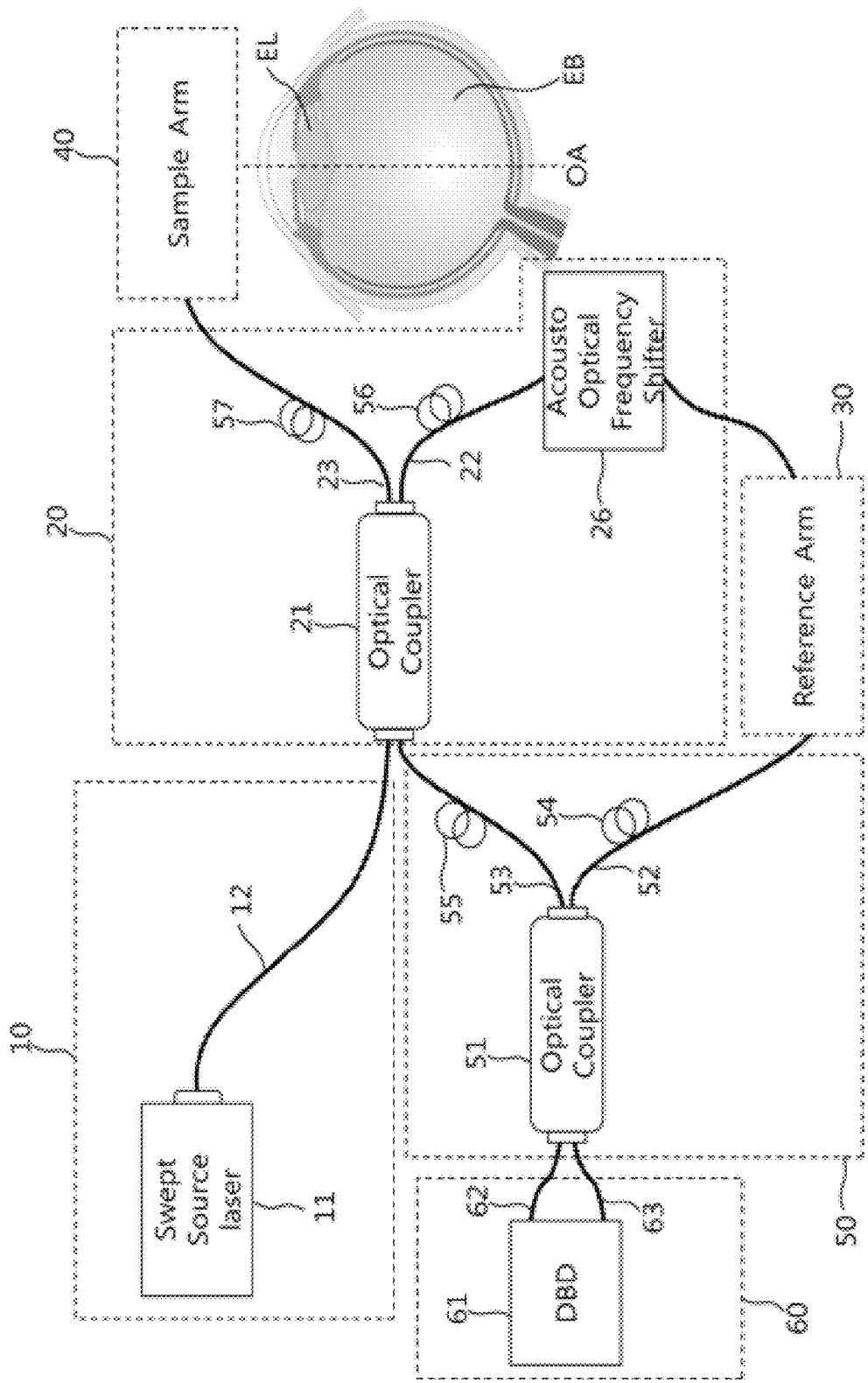

FIGS. 2 and 3 are block diagrams illustrating an optical coherence tomography system for ocular diagnosis according to one embodiment of the present invention.

As illustrated in FIGS. 2 and 3, the optical coherence tomography system includes: a light source unit 10 generating and transmitting light L; a light distribution unit 20 dividing the transmitted light L into first light L1 and second light L2; a reference arm 30 generating first reference light RL1 and second reference light RL2, whose optical path length is larger than that of the first reference light, from the first light L1; a sample arm 40 irradiating the second light L2 onto a central optical axis OA directed towards the central portion of the eye lens EL to generate first measurement light SL1 and irradiating the second light L2 onto the eye lens EL in an oblique direction inclined with respect to the central optical axis OA at a time different from the time when the first measurement light SL1 is generated, to generate second measurement light SL2; an interference unit 50 allowing the first reference light RL1 to interfere with the first measurement light SL1 and the second reference light RL2 to interfere with the second measurement light SL2 to generate corresponding interference signals; and a detection unit 60 converting the interference signals into electrical signals.

The present invention is directed to an optical coherence tomography (OCT) system that can be used in the field of ophthalmology. OCT systems are diagnostic imaging devices for high-resolution imaging of internal microstructures in living tissue based on optical interference. OCT systems can acquire high-resolution sectional images of living tissue in a non-invasive manner and are thus used for clinical or therapeutic purposes in dermatology, ophthalmology, internal medicine, dentistry, and other medical specialties. OCT is utilized for the diagnosis of diseases of the anterior segment of the eye, intraocular lens implantation, etc. in the field of ophthalmology. Conventional OCT systems fail to directly acquire tomography images of the peripheral portion of the eye lens hidden by the iris due to the structure of the anterior segment of the eye in which the iris is located in front of the peripheral portion of the eye lens. Conventional OCT systems have problems in that they suffer from difficulty in reliably diagnosing diseases of the anterior segment of the eye and cannot accurately determine morphological parameters of the eye lens, such as diameter, volume, surface area, curvature, asphericity, slope, decenterization, and internal structure, for intraocular lens implantation and prognostic observation. The present invention has been made in an effort to solve these problems.

Specifically, the optical coherence tomography system includes a light source unit 10, a light distribution unit 20, a reference arm 30, a sample arm 40, an interference unit 50, and a detection unit 60.

The light source unit 10 includes a coherence light source 11 and generates and outputs broadband light L. The light source 11 may be, for example, a swept source laser, but is not necessarily limited thereto. The light source is not particularly limited as long as it can generate and output light in a wavelength region where a topography image of the eyeball can be taken. The light L output from the light source unit 10 is transmitted to the light distribution unit 20 through an optical fiber 12.

The light distribution unit 20 divides the light L transmitted through the optical fiber of the light source unit 10 into first light L1 and second light L2. A tunable optical coupler 21 can be used as means to divide the light L. However, the use of the optical coupler 21 is not necessarily required to divide the light L. Any means capable of splitting the incident light L into several beams and outputting the split beams may be used without particular limitation as the optical coupler 21. The first light L1 is transmitted to the reference arm 30 and the second light L2 is transmitted to the sample arm 40. The first light L1 can be delivered to the reference arm 30 through an optical fiber 22 connecting the optical coupler 21 and the reference arm 30 and the second light L2 can be delivered to the sample arm 40 through an optical fiber 23 connecting the optical coupler 21 and the sample arm 40. An acousto optic frequency shifter (AOFS) 26 is arranged in the optical fiber 22 connecting the optical coupler 21 and the reference arm 30 to selectively shift the frequency of the first light L1.

The reference arm 30 receives the first light L1 divided and transmitted from the light distribution unit 20 to generate first reference light RL1 and second reference light RL2. The first reference light RL1 and the second reference light RL2 are distinguished by their different optical path lengths. The second reference light RL2 has a relatively large optical path length. The first reference light RL1 and the second reference light RL2 are transmitted to the interference unit 50.

The sample arm 40 receives the second light L2 divided and transmitted from the light distribution unit 20 to generate first measurement light SL1 and second measurement light SL2. The sample arm 40 irradiates the second light L2 toward the eye lens EL. The irradiation direction of the second light L2 may be changed. The second light L2 may be irradiated along a central optical axis OA directed towards the central portion of the eye lens EL. Alternatively, the second light L2 may be irradiated in an oblique direction inclined at an angle with respect to the central optical axis OA. Here, the central optical axis OA corresponds to the thickness direction of the central portion of the eye lens EL. The first measurement light SL1 is generated when the second light L2 is irradiated and reflected along the central optical axis OA and the second measurement light SL2 is generated when the second light L2 is irradiated and reflected in the oblique direction. The first measurement light SL1 and the second measurement light SL2 are not generated simultaneously and the first measurement light SL1 is generated at a time different from the time when the second measurement light SL2 is generated because the sample arm 40 irradiates the second light L2 while changing the direction of propagation of the second light L2. The second light L2 may be irradiated continuously rather than intermittently. That is, the second light L2 may be irradiated by increasing or decreasing the angle between the central optical axis OA and the oblique direction. When irradiated continuously, the second light L2 can move along the direction from one lateral end to the other lateral end of the eye lens EL through the center thereof. When irradiated in an oblique direction inclined with respect to the central optical axis OA, the second light L2 can approach the eye lens EL in a direction inclined relative to the iris, with the result that it can reach the lateral end of the eye lens EL. Hence, an image of the whole eye lens EL can be acquired because the second light L2 can scan the entire area of the eye lens EL.

The first measurement light SL1 and the second measurement light SL2 generated after the second light L2 is incident on and reflected from the eyeball EB are delivered to the light distribution unit 20 in the reverse order to that of the propagation path of the second light L2. In this case, the first measurement light and the second measurement light may enter the optical coupler 21 through the optical fiber 23 of the light distribution unit 20.

The interference unit 50 generates interference signals from the first measurement light SL1, the second measurement light SL2, the first reference light RL1, and the second reference light RL2. The interference signals are obtained by interference of the first reference light RL1 with the first measurement light SL1 or interference of the second reference light RL2 with the second measurement light SL2. The interference unit consists of an optical coupler 51, an optical fiber 52 connecting the optical coupler 51 and the reference arm 30, and an optical fiber 53 connecting the optical coupler 51 and the light distribution unit 20. The first reference light RL1 and the second reference light RL2 are delivered from the reference arm 30 to the optical coupler 51 through the optical fiber 52 and the first measurement light SL1 and the second measurement light SL2 are delivered to the optical coupler 51 via the optical coupler 21 of the light distribution unit and the optical fiber 53. As a result, interference of the first reference light RL1 with the first measurement light SL1 or interference of the second reference light RL2 with the second measurement light SL2 occurs in the optical coupler 51. The interference unit 50 includes a plurality of polarization controllers 54, 55, 56, and 57 to control the intensities of interference when the first measurement light SL1 and the second measurement light SL2 meet the first reference light RL1 and the second reference light RL2, respectively. Here, the polarization controllers 54 and 55 are arranged in the optical fibers 52 and 53 of the interference unit 50, respectively, and the polarization controllers 56 and 57 are arranged in the optical fibers 22 and 23 of the light distribution unit 20, respectively. The interference intensities can be controlled to reach their maximum values by the polarization controllers 54, 55, 56, and 57.

The detection unit 60 receives the interference signals and converts the interference signals into electrical signals to obtain coherence tomography images of the anterior segment of the eye. The detection unit 60 includes a balanced photodetector (BPD) 61 connected to the interference unit 50 through optical fibers 62 and 63. The balanced photodetector (BPD) 61 can detect the interference signals received from the interference unit 50.

Overall, the optical coherence tomography system of the present invention is constructed such that light is irradiated onto the eye lens in an oblique direction toward the eye lens as well as in a direction perpendicular to the eye lens. Due to this construction, the optical coherence tomography system of the present invention can generate measurement light by one-time scanning so that optical coherence tomography images of the whole anterior segment of the eye including peripheral portions hidden by the iris can be obtained. Therefore, the optical coherence tomography system of the present invention can be used to accurately diagnose diseases of the anterior segment of the eye, show the morphology of the whole eye lens, and monitor the eye lens in real time. Due to these advantages, the optical coherence tomography system of the present invention can be utilized as a powerful diagnostic tool for observing prognosis of intraocular lens implantation.

The present invention will be described in detail with reference to exemplary embodiments of the reference arm 30 and the sample arm 40.

Figure 4:
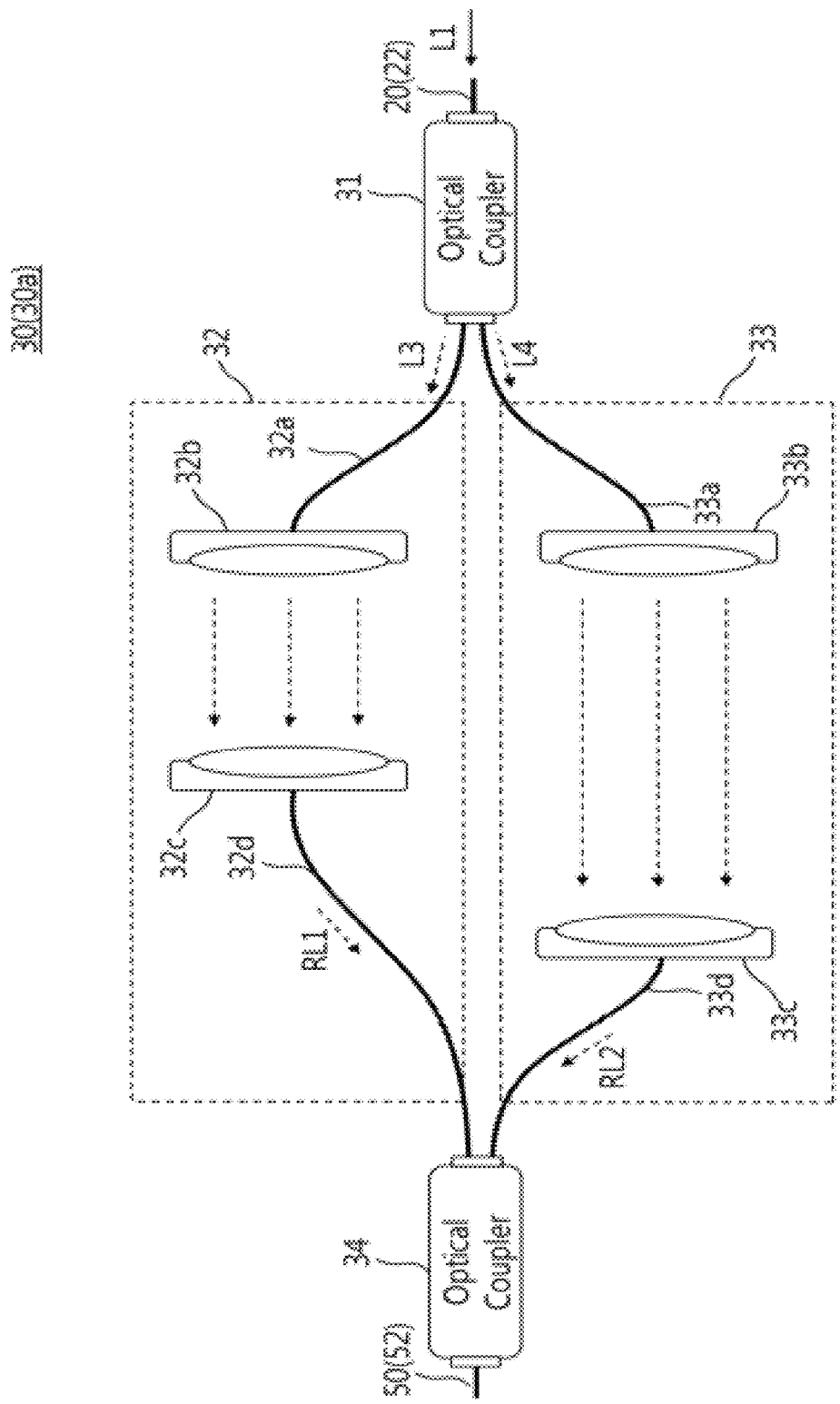
FIG. 4 is a diagram illustrating the constitution of one embodiment of the reference arm illustrated in FIGS. 2 and 3.

FIG. 4 is a diagram illustrating the constitution of one embodiment of the reference arm illustrated in FIGS. 2 and 3.

As illustrated in FIG. 4, the reference arm 30 or 30a may include a first reference arm optical coupler 31, a first reference light output unit 32, and a second reference light output unit 33.

The first reference arm optical coupler 31 receives the first light L1 from the light distribution unit 20 and divides the received first light L1 into third light L3 and fourth light L4. For example, the first light L1 may enter the first reference arm optical coupler 31 through the optical fiber 22 connecting the optical coupler 21 of the light distribution unit 20 (see FIG. 3) and the first reference arm optical coupler 31 and divided into third light L3 and fourth light L4 by the first reference arm optical coupler 31.

The first reference light output unit 32 generates and outputs the first reference light RL1 from the third light L3. To this end, the first reference light output unit 32 includes a first reference arm optical fiber 32a, a first reference arm collimator 32b, a second reference arm collimator 32c, and a second reference arm optical fiber 32d. One end of the first reference arm optical fiber 32a is connected to the first reference arm optical coupler 31 and the other end thereof is connected to the first reference arm collimator 32b. Thus, the third light L3 divided by the first reference arm optical coupler 31 enters the first reference arm collimator 32b through the first reference arm optical fiber 32a. The third light L3 is converted into parallel light in the first reference arm collimator 32b and the parallel light exits from the first reference arm collimator 32b. The second reference arm collimator 32c is spaced a first distance from the first reference arm collimator 32b. With this arrangement, the parallel light exiting from the first reference arm collimator 32b enters the second reference arm collimator 32c where the first reference light RL1 is generated, and the optical path length of the first reference light RL1 is determined by the distance between the first reference arm collimator 32b and the second reference arm collimator 32c. The first reference light RL1 is output through the second reference arm optical fiber 32d whose one end is connected to the second reference arm collimator 32c.

The second reference light output unit 33 generates and outputs the second reference light RL2 from the fourth light L4. Specifically, the second reference light output unit 33 includes a third reference arm optical fiber 33a, a third reference arm collimator 33b, a fourth reference arm collimator 33c, and a fourth reference arm optical fiber 33d. One end of the third reference arm optical fiber 33a is connected to the first reference arm optical coupler 31 and the other end thereof is connected to the third reference arm collimator 33b. Thus, the fourth light L3 divided by the first reference arm optical coupler 31 enters the third reference arm collimator 33b through the third reference arm optical fiber 33a. The fourth light L4 is converted into parallel light in the third reference arm collimator 33b and the parallel light exits from the third reference arm collimator 33b. The fourth reference arm collimator 33c is spaced a second distance from the third reference arm collimator 33b. With this arrangement, the parallel light exiting from the third reference arm collimator 33b enters the fourth reference arm collimator 33c where the second reference light RL2 is generated. Here, the optical path length of the second reference light RL2 is determined by the second distance between the third reference arm collimator 33b and the fourth reference arm collimator 33c. Since the second distance is longer than the first distance, the optical path length of the second reference light RL2 is larger than that of the first reference light RL1. The second reference light RL2 is output through the fourth reference arm optical fiber 33d whose one end is connected to the fourth reference arm collimator 33c.

The output first reference light RL1 and second reference light RL2 are delivered to the interference unit 50. Here, the first reference light RL1 and the second reference light RL2 can be combined into one in a second reference arm optical coupler 34 and delivered to the interference unit 50 (for example, the optical fiber 52 connected to the optical coupler 51 of the interference unit 50 illustrated in FIG. 3).

Figure 5:
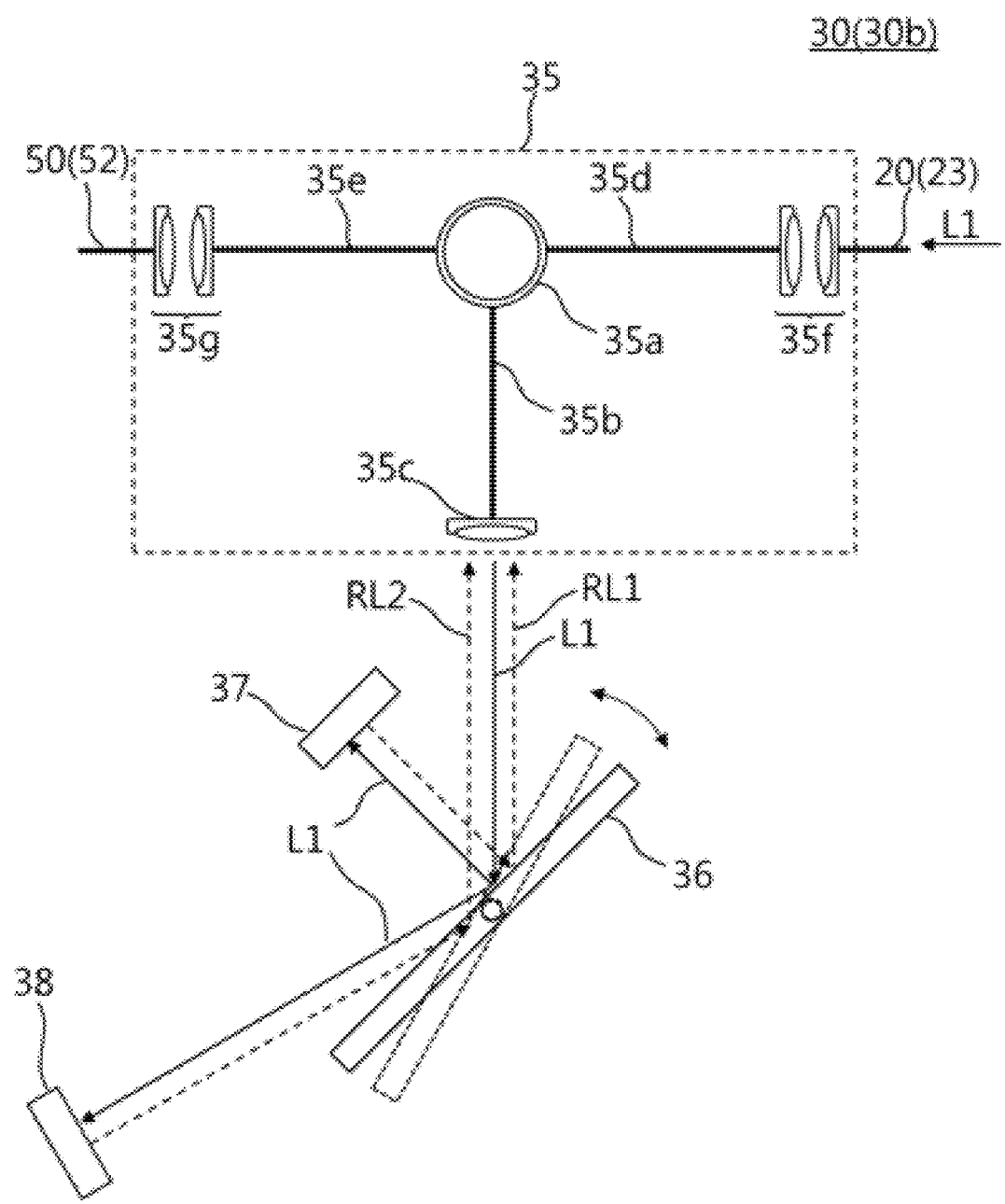
FIG. 5 is a diagram illustrating the constitution of another embodiment of the reference arm illustrated in FIGS. 2 and 3.

FIG. 5 is a diagram illustrating the constitution of another embodiment of the reference arm illustrated in FIGS. 2 and 3.

Referring to FIG. 5, the reference arm 30 or 30b includes a light delivery unit 35, a reference arm scanning mirror 36, a first reflective mirror 37, and a second reflective mirror 38.

The light delivery unit 35 receives the first light L1 and controls the delivery of the first light L1, reference light RL1, and reference light RL2. To this end, the light delivery unit 35 may include an optical circulator 35a, a first reference arm optical fiber and a reference arm collimator 35c. The optical circulator 35a receives the first light L1 from the light distribution unit 20, for example, from the optical fiber 23 connected to the optical coupler 21 illustrated in FIG. 3, and controls the delivery of the light. The optical circulator 35a can control the delivery of the entering first light L1, reference light RL1, and reference light RL2 due to its ability to deliver light to a desired location and block the delivery of light to an undesired location. The first reference arm optical fiber having one end connected to the optical circulator 35a provides a path through which the first light L1 having passed through the optical circulator 35a is transmitted. The reference arm collimator 35c connected to the other end of the first reference arm optical fiber 35b converts the first light L1 into parallel light and emits the parallel light.

The reference arm scanning mirror 36 changes the direction of propagation of the first light L1 exiting from the reference arm collimator 35c. The angle of reflection of the first light L1 is controlled by the rotating reference arm scanning mirror 36 so that the direction of propagation of the first light L1 can be changed.

The first reflective mirror 37 is arranged at a location on which the first light L1 reflected at a first angle of rotation of the reference arm scanning mirror 36 is vertically incident, such that the first light L1 reflected from the reference arm scanning mirror 36 is reflected back to the reference arm scanning mirror 36 to generate first reference light RL1. Here, the first reflective mirror 37 is spaced a first distance from the reference arm scanning mirror 36. The optical path length of the first reference light RL1 is determined by the first distance.

The second reflective mirror 38 is arranged at a location on which the first light L1 reflected at a second angle of rotation of the reference arm scanning mirror 36 is vertically incident. With this arrangement, the first light L1 incident on the second reflective mirror 38 is reflected to the reference arm scanning mirror 36 to generate second reference light RL2. Here, since the second reflective mirror 38 is spaced a second distance larger than the first distance from the reference arm scanning mirror 36, the optical path length of the second reference light RL2 is larger than that of the first reference light RL1.

On the other hand, the first reference light RL1 and the second reference light RL2 are incident on and reflected from the reference arm scanning mirror 36, enter the reference arm collimator 35c, and are delivered to the interference unit 50 through the first reference arm optical fiber 35b and the optical circulator 35a. A pair of collimators 35f are arranged to face each other between the end of the optical fiber 23 of the light distribution unit 20 (see FIG. 3), through which the first light L1 propagates, and the end of the optical fiber 35d connected to the optical circulator 35a. A pair of collimators 35g are arranged to face each other between the end of the optical fiber 35e connected to the optical circulator 35a, through which the first reference light RL1 and the second reference light RL2 propagate, and the end of the optical fiber 52 of the interference unit 50.

Figure 6:
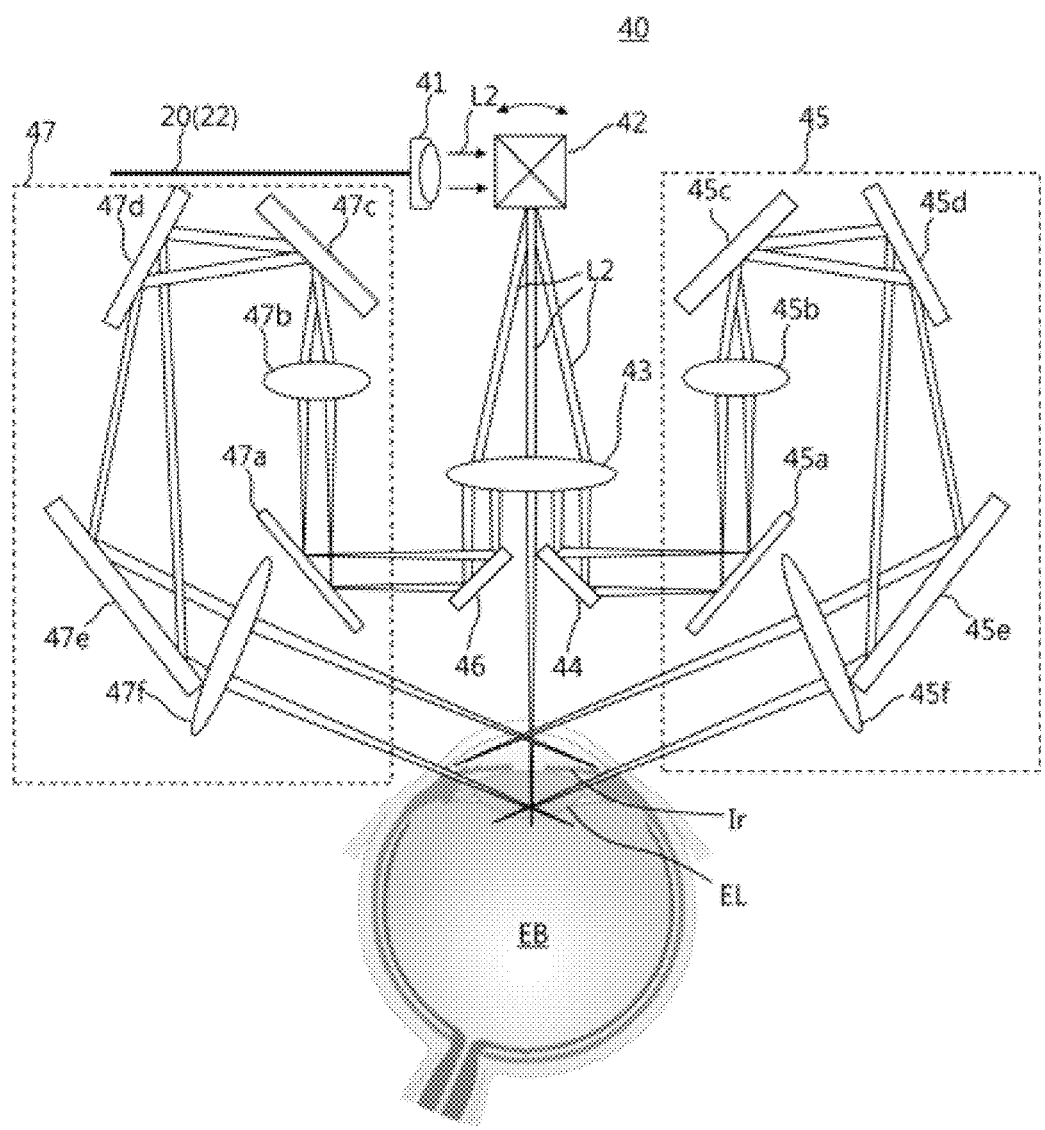
FIG. 6 is a diagram illustrating the constitution of one embodiment of the sample arm illustrated in FIGS. 2 and 3.

FIG. 6 is a diagram illustrating the constitution of one embodiment of the sample arm illustrated in FIGS. 2 and 3.

As illustrated in FIG. 6, the sample arm 40 includes a sample arm collimator 41, a sample arm scanning mirror 42, a first scanning lens 43, a first outwardly reflective mirror 44, and a first reflection system 45.

The sample arm collimator 41 is connected to the end of the optical fiber 22 of the light distribution unit 20 through which the second light L2 is delivered. The sample arm collimator 41 converts the second light L2 into parallel light and emits the parallel light.

The sample arm scanning mirror 42 continuously changes the direction of propagation of the emitted second light L2. The direction of propagation of the second light L2 can be changed by controlling the angle of rotation of the sample arm scanning mirror 42.

The second light L2 reflected from the sample arm scanning mirror 42 is concentrated through the first scanning lens 43. The first scanning lens 43 has a curved central portion arranged on the central optical axis OA directed towards the central portion of the eye lens EL of the eyeball EB (see FIG. 3). With this arrangement, the second light L2 transmitted through the curved central portion of the first scanning lens 43 after its direction of propagation is controlled by the sample arm scanning mirror 42 is irradiated onto the central portion of the eye lens EL. The irradiated second light L2 is reflected from the central portion of the eye lens EL to generate first measurement light.

The first outwardly reflective mirror 44 is arranged between a curved peripheral portion surrounding the curved central portion of the first scanning lens 43 and the eye lens EL. With this arrangement, the second light L2 transmitted through the curved peripheral portion of the first scanning lens 43 after its direction of propagation is controlled by the sample arm scanning mirror 42 is incident on the first outwardly reflective mirror 44. The first outwardly reflective mirror 44 has a plane of reflection inclined relative to the plane of incidence of the second light L2. This arrangement allows the first outwardly reflective mirror 44 to reflect the second light L2 in a lateral direction outward from the eye lens EL.

The first reflection system 45 receives the second light L2 reflected from the first outwardly reflective mirror 44 and reflects the second light L2 in a first oblique direction toward the eye lens EL from the outside the eye lens EL. Here, the rotation of the sample arm scanning mirror 42 allows the second light L2 irradiated in the first oblique direction to scan the eye lens EL. The second light L2 is reflected from the eye lens EL to generate second reference light.

The first reflection system 45 includes a first mirror 45a, a first lens 45b, a second mirror 45c, a third mirror 45d, a fourth mirror 45e, and a second lens 45f.

The second light L2 reflected from the first outwardly reflective mirror 44 is incident on and reflected from the first mirror 45a and is concentrated through the first lens 45b. When the concentrated second light L2 is incident on and reflected from the second mirror 45c, its direction of propagation is changed. The second light L2 reflected from the second mirror 45c is incident on and reflected from the third mirror 45d and is then incident on the fourth mirror 45e. The second light L2 is reflected from the fourth mirror 45e and propagates in the first oblique direction. The second light L2 propagating in the first oblique direction is concentrated through the second lens 45f and irradiated onto the anterior segment of the eye. The second light L2 irradiated in the first oblique direction can scan even portions of the eye lens EL that are hidden by the iris Ir when irradiated in the vertical direction (along the central optical axis).

The sample arm 40 may further include a second outwardly reflective mirror 46 and a second reflection system 47.

The second outwardly reflective mirror 46 is arranged so as to be symmetric to the first outwardly reflective mirror 44 with respect to the central optical axis and reflects the second light L2 transmitted through the curved peripheral portion in a lateral direction outward from the eye lens EL.

The second reflection system 47 can reflect the second light L2 reflected from the second outwardly reflective mirror 46 in a second oblique direction toward the eye lens EL from the outside of the eye lens EL.

The second reflection system 47 can be constructed corresponding to the first reflection system 45. Specifically, the second reflection system 47 includes a first mirror 47a, a first lens 47b, a second mirror 47c, a third mirror 47d, a fourth mirror 47e, and a second lens 47f.

The second light L2 reflected from the second outwardly reflective mirror 46 is incident on and reflected from the first mirror 47a and is concentrated through the first lens 47b. When the concentrated second light L2 is reflected from the second mirror 47c, its direction of propagation is changed. The second light L2 reflected from the second mirror 47c is incident on and reflected from the third mirror 47d and is then incident on the fourth mirror 47e. The second light L2 is reflected from the fourth mirror 47e and propagates in the second oblique direction. The second light L2 propagating in the second oblique direction is concentrated through the second lens 47f and irradiated onto the anterior segment of the eye. The second light L2 irradiated in the second oblique direction can scan even portions of the eye lens EL that are hidden by the iris Ir when irradiated in the vertical direction (along the central optical axis) and even portions of the eye lens EL that are not scanned when irradiated in the first oblique direction.

Although the present invention has been described herein with reference to the specific embodiments, these embodiments do not serve to limit the invention and are set forth for illustrative purposes. It will be apparent to those skilled in the art that modifications and improvements can be made without departing from the spirit and scope of the invention.

Such simple modifications and improvements of the present invention belong to the scope of the present invention, and the specific scope of the present invention will be clearly defined by the appended claims.

What is claimed is:

1. An optical coherence tomography system for ocular diagnosis, comprising:
    a light source unit generating and transmitting light;
    a light distribution unit dividing the transmitted light into first light and second light;
    a reference arm generating first reference light and second reference light, whose optical path length is larger than that of the first reference light, from the first light;
    a sample arm irradiating the second light onto a central optical axis directed towards the central portion of the eye lens to generate first measurement light and irradiating the second light onto the eye lens in an oblique direction inclined with respect to the central optical axis at a time different from the time when the first measurement light is generated, to generate second measurement light;
    an interference unit allowing the first reference light to interfere with the first measurement light and the second reference light to interfere with the second measurement light to generate corresponding interference signals; and
    a detection unit converting the interference signals into electrical signals,
    wherein the sample arm comprises:
    a sample arm collimator connected to one end of an optical fiber through which the second light from the light distribution unit is transmitted;
    a sample arm scanning mirror continuously changing the direction of propagation of the second light exiting from the sample arm collimator;
    a first scanning lens through which the second light reflected from the sample arm scanning mirror is transmitted and whose curved central portion is arranged on the central optical axis;
    a first outwardly reflective mirror arranged between a curved peripheral portion surrounding the curved central portion of the first scanning lens and the eye lens to reflect the second light transmitted through the curved peripheral portion in a lateral direction outward from the eye lens; and
    a first reflection system reflecting the second light reflected from the first outwardly reflective mirror in a first oblique direction toward the eye lens from the outside of the eye lens.

2. The optical coherence tomography system according to claim 1, wherein the first reflection system comprises:
    a first mirror reflecting the second light reflected from the first outwardly reflective mirror;
    a first lens through which the second light reflected from the first mirror is transmitted;
    a second mirror reflecting the second light transmitted through the first lens;
    a third mirror reflecting the second light reflected from the second mirror;
    a fourth mirror reflecting the second light reflected from the third mirror in the first oblique direction; and
    a second lens through which the second light reflected from the fourth mirror is transmitted.

3. The optical coherence tomography system according to claim 1, wherein the sample arm further comprises:
    a second outwardly reflective mirror arranged so as to be symmetric to the first outwardly reflective mirror with respect to the central optical axis and reflecting the second light transmitted through the curved peripheral portion in a lateral direction outward from the eye lens; and
    a second reflection system reflecting the second light reflected from the second outwardly reflective mirror in a second oblique direction toward the eye lens from the outside of the eye lens.

4. The optical coherence tomography system according to claim 3, wherein the second reflection system comprises:
    a first mirror reflecting the second light reflected from the second outwardly reflective mirror;
    a first lens through which the second light reflected from the first mirror is transmitted;
    a second mirror reflecting the second light transmitted through the first lens;
    a third mirror reflecting the second light reflected from the second mirror;
    a fourth mirror reflecting the second light reflected from the third mirror in the second oblique direction; and a second lens through which the second light reflected from the fourth mirror is transmitted.

* * * * *